United States Patent [19]
Gertzman et al.

[11] Patent Number: 4,620,541
[45] Date of Patent: Nov. 4, 1986

[54] ANNEALED POLYDIOXANONE SURGICAL DEVICE HAVING A RESILIENT PORTION AND AN INTERLOCKING PORTION AND METHOD FOR PRODUCING THE SAME

[75] Inventors: Arthur A. Gertzman, Bridgewater; Darrell R. Thompson, Somerville, both of N.J.

[73] Assignee: Ethicon, Inc., Somerville, N.J.

[21] Appl. No.: 761,650

[22] Filed: Aug. 2, 1985

Related U.S. Application Data

[63] Continuation-in-part of Ser. No. 436,224, Oct. 25, 1982, abandoned, which is a continuation-in-part of Ser. No. 288,275, Jul. 30, 1981, abandoned.

[51] Int. Cl.[4] ............................................. A61B 17/12
[52] U.S. Cl. ................... 128/326; 128/335.5; 128/346
[58] Field of Search ............ 128/325, 326, 92 B, 128/303 R, 335.5; 206/339

[56] References Cited

U.S. PATENT DOCUMENTS

| | | | |
|---|---|---|---|
| 4,032,993 | 7/1977 | Coquard et al. | 128/335.5 |
| 4,052,988 | 10/1977 | Doddi et al. | 128/92 B |
| 4,412,617 | 11/1983 | Cerwin | 206/339 |
| 4,418,694 | 12/1983 | Beroff et al. | 128/325 |
| 4,424,810 | 1/1984 | Jewusiak | 128/326 |

Primary Examiner—C. Fred Rosenbaum
Assistant Examiner—Jerome R. Smith, Jr.
Attorney, Agent, or Firm—Robert L. Minier

[57] ABSTRACT

Thermally formed annealed surgical devices made from unoriented polymers of p-dioxanone and methods for manufacturing the same. The preferred device is a ligating clip having good in vivo performance characteristics. The method includes initially drying the thermally formed device followed by heating the device without restraint at specific temperatures for specific time periods.

8 Claims, 5 Drawing Figures

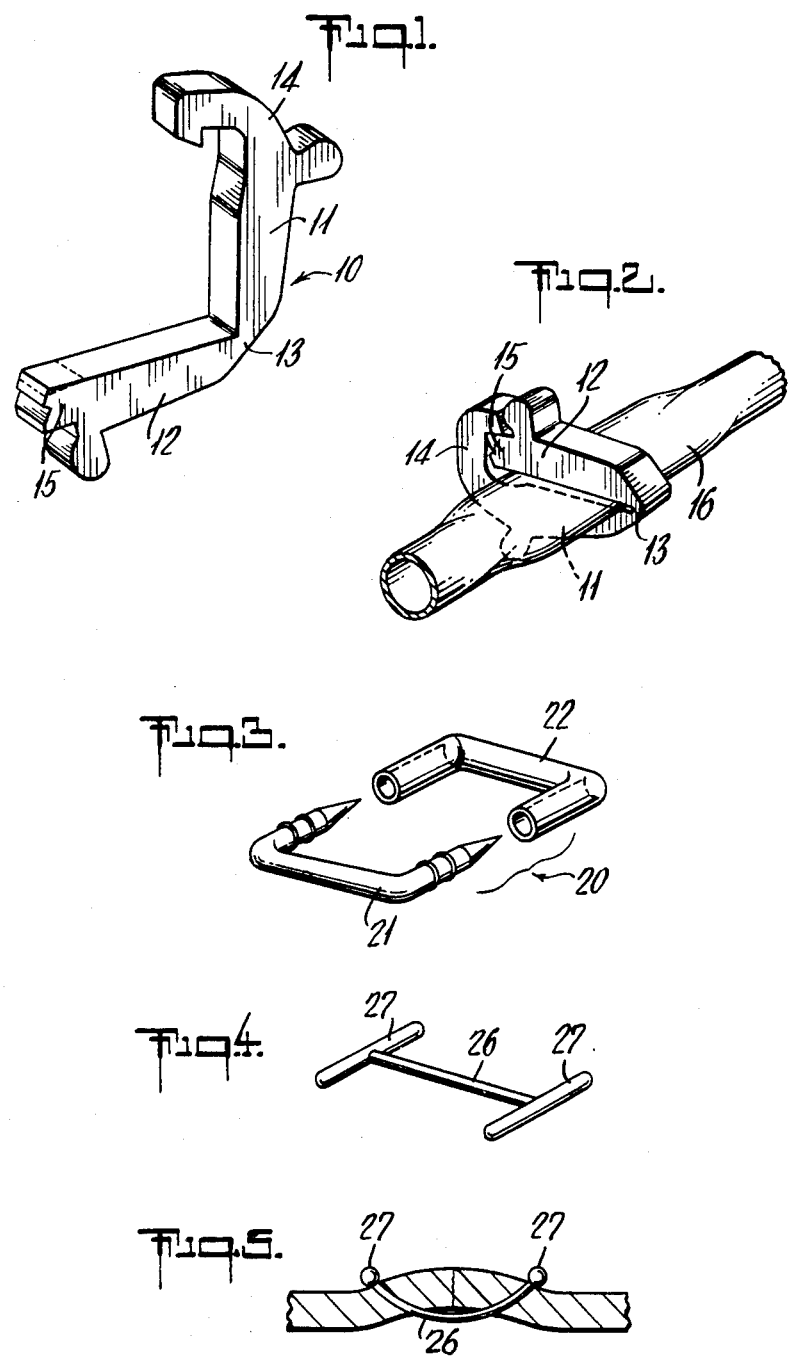

ANNEALED POLYDIOXANONE SURGICAL DEVICE HAVING A RESILIENT PORTION AND AN INTERLOCKING PORTION AND METHOD FOR PRODUCING THE SAME

RELATED APPLICATION

The present application is a continuation-in-part application of patent application Ser. No. 436,224 abandoned filed Oct. 25, 1982 which is a continuation-in-part application of patent application Ser. No. 288,275 filed July 30, 1981, now abandoned.

BACKGROUND OF THE INVENTION

The present invention relates to surgical devices made from polymers of p-dioxanone and more particularly to molded surgical devices of such polymers having improved in vivo performance characteristics.

It is well known that in many and various surgical procedures synthetic devices, that is, devices made from foreign materials, are very often implanted. Examples of such procedures are in surgery wherein tantalum or stainless steel or other metal clips are used to control bleeding by ligating various blood vessels or other tubular organs during the surgical procedure. Furthermore, in other surgical procedures, various other fasteners, staples or clips are implanted for various fastening support or other reasons during a surgical procedure. In most instances, these devices remain in the patient for considerable periods of time, though in some instances, they may be removed at some later date or even rejected by the natural physiological function of the human body.

For the most part these metal surgical devices, even though they may cause no harm from the medical viewpoint, it is desired they not be allowed to remain in the body as they greatly disrupt the post-operative x-ray procedures and subsequent diagnostic imaging of the patient. The metal materials not only disrupt X-ray imaging, but they also disrupt the newer computerized axial tomography imaging, and other of the new types of diagnostic imaging procedures. Hence, it is desirous that the surgical devices be replaced by non-metallic, bio-compatible materials which do not have a disruptive effect on the new diagnostic imaging procedures. It is even more desirable to make the medical devices, in many instances, out of absorbable polymers so that once they have completed the desired function, they are absorbed by the human body, and, hence, have no subsequent effect on diagnostic imaging or the like. Devices made from absorbable polymers also prevent any long term complications which might arise from having a foreign body present in the tissue.

Surgical devices and the desired absorbable polymers are more fully disclosed in U.S. Pat. No. 4,052,988 issued Oct. 11, 1977 and incorporated herein by reference. A specific process for making such a desirable surgical device made from these absorbable polymers is disclosed in co-pending commonly assigned patent application Ser. No. 288,275, filed July 30, 1981. In that case, there is described a process of producing a molded surgical device from polymers of p-dioxanone. Though surgical devices produced in accordance with the method described in the above mentioned patent application have desired strength and other properties for many surgical procedures, it is still important to even further improve the strength, functional integrity, flexibility, and especially the tactile and audible properties of surgical devices made from these polymers. These improved properties expands the potential usage of the devices and improves their reliability, stability and the in vivo performance of such surgical devices.

Many surgical devices used in various procedures start in one position, i.e., an open position, and when in the proper place are put in a second position; i.e., a closed position. For example, a hemostatic clip is placed about a vessel to be closed with the clip in an open position. Once the clip is properly placed, the clip is closed to shut off the vessel. Many of these devices which have their position modified during use are used in areas where visibility may be a problem and the surgeon must rely on other senses such as feeling and hearing in order to properly place the device. Hence, it is often desired that such devices have both tactile and audible properties to assist the surgeon when using the device. Tactile properties are placed in the device by providing some resilient portion in the device; i.e., a portion which resists the movement of the device from one position to another position. For example, in a hemostatic clip the resilient portion may be a hinge which holds the clip in an open position and which resiliency must be overcome to close the clip, thus providing the user with some tactile "feedback" as the clip is closed. Audible properties may result from some interlocking or interengaging of parts once the device is placed in a desired position, i.e., the parts snap together with a sound that can be heard by the user to let the user know the device has been placed in the desired position.

Also, in U.S. Pat. No. 4,025,988 there is described an annealing procedure useful for sutures to improve desirable properties of the sutures. The suture to be annealed is an oriented filament. The oriented filament is held under restraint while being annealed and the molecular configuration of the oriented product altered to improve the desired strength properties of the suture.

SUMMARY OF THE PRESENT INVENTION

What we have discovered is an annealing or heat treating process for thermally formed, substantially unoriented, surgical devices made from the polymers of p-dioxanone, which improves the strength and functional integrity of the device while also improving the audible and tactile properties of the device. By the phrase "surgical devices having audible and tactile properties" it is meant a device having a resilient portion which provides some "feedback" to the feel of the user and interengaging portions which provide a "snap" which can be heard by the user. The audible and tactile properties of the device may be further explained by understanding that in many surgical procedures the surgeon works in an area of limited vision. When so working, an advantage our clip has over the prior art clips is that the surgeon may rely on feeling and hearing to know when a specific step of the surgical procedure has been accomplished. For example, in closing off a blood vessel with a latching type clip, the surgeon may not see this step and, hence, may rely on the resistance to closing of the clip (the tactile property) and a click or snap when the latch closes (the audible property). We have discovered that our new process unexpectedly improves these properties in surgical devices made from the polymers of p-dioxanone. Our new process also produces a surgical device having improved shelf-life in that the device is more resistant to hydrolysis caused by residual moisture in the package.

By "substantially unoriented" it is meant that the device has not been subjected to any process steps such as drawing or the like that would increase the molecular orientation of the p-dioxanone polymer. By the term "annealed" it is meant a heat treatment followed by cooling to modify the properties of the product so treated. In accordance with the present invention, our new method for treating a thermally formed surgical device made from polymers of p-dioxanone to improve both the properties described previously comprises: drying the thermally formed device under a nitrogen purge at a temperature not to exceed 30° C. for a period of time sufficient to substantially remove all moisture from the device. The dried device is heated, without any restraint, in an oxygen-free, inert, dry atmosphere, preferably an atmosphere of nitrogen, at a temperature of 50° C. to 90° C. and preferably at a temperature of from 80° to 85° C. for at least 7 hours.

The resultant new products of the present invention comprise thermally formed, substantially unoriented, annealed, surgical devices made from polymers of p-dioxanone having a density of at least 1.384 grams per cubic centimeter and a crystallinity of at least 43% and preferably of at least 45%.

DESCRIPTION OF THE DRAWINGS

FIG. 1 is an enlarged perspective view of a ligating clip in accordance with the present invention;

FIG. 2 is an enlarged perspective view showing the clip of FIG. 1 in place closing off a blood vessel;

FIG. 3 is an enlarged perspective view of yet another surgical device in accordance with the present invention;

FIG. 4 is a perspective view of yet another surgical device in accordance with a present invention; and FIG. 5 is a cross-sectional view showing the device of FIG. 4 in place in closing the wound.

DETAILED DESCRIPTION OF THE EMBODIMENTS

The new surgical devices of the present invention are made from polymers comprised of units having the general formula

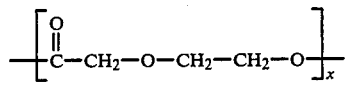

wherein x is the degree of polymerization resulting in the desired polymer.

The polymer is prepared from a monomer having the following formula:

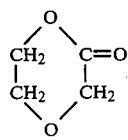

Generally, the surgical devices of the present invention are produced by injection molding techniques. A specific and preferred method of injection molding is described in co-pending commonly assigned patent application Ser. No. 288,275 filed July 30, 1981 and incorporated herein by reference. Though the surgical devices are described as being made by injection molding, they may also be made by compression molding or extrusion molding and the like. The polymers after molding are dried to remove substantially all of the moisture in the molded article. The polymers are dried with a nitrogen purge at a temperature of less than 30° C. so that substantially all moisture is removed to reduce the possible hydrolysis of the absorbable polymer.

Once the molded article is dried, it is placed in an atmosphere of a dry, inert, oxygen free gas preferably and for the sake of economics, nitrogen, although other dry inert gases may also be used. The molded article in the dry inert atmosphere is heated to a temperature of at least 50° C. but not in excess of 90° C. and preferably at a temperature of from 80° to 85° C., for a period of time of at least 7 hours. The device is placed under no restraint during this heating operation. The molded article is then packaged, sterilized, dried and is ready for use. Generally, the polymers used in accordance with the present invention are sterilized by ethylene oxide treatment as is well known in the art. We have found that the process described above improves the strength of various configurations used in the surgical devices. Not only does it improve the baseline or initial strength of the device but also it reduces the amount of strength the device loses with time in vivo. Our annealing process also improves both the tactile and audible responses of surgical devices made in accordance with our process and enhances their hydrolytic resistance so that the shelf life of the device is considerably improved. It is believed that our annealing process produces crystallites within the molded article which enhances its resistance to hydrolysis and improves the strength and functional integrity of the molded device. Our new surgical devices made from the polymers and copolymers of p-dioxanone have a density of at least 1.3845 grams per cubic centimeter. It is imperative the device have this density in order to have the improved properties described herein. Furthermore, our new surgical devices have a crystallinity of at least 43% and preferably 45%.

The crystallinity of the clip is a measurement of the strength and functional integrity of the clip. X-ray diffraction is a convenient method of determining the amount and type of crystallinity in the clip. The X-ray crystallinity data is obtained using a Phillips vertical goniometer equipped with a graphite crystal monochrometer and scintillation detector interfaced to a strip chart recorder. CuKα radiation is employed and a sample is mounted and run using parafocusing geometry. The patterns obtained for a sample are analyzed for crystallinity and amorphous content using a DuPont Curve Resolver.

Referring to the drawings, there is depicted certain specific types of surgical devices of the present invention which may be made by the method of the present invention. In FIG. 1, there is shown a ligating clip 10. This clip is used to ligate a blood vessel during various surgical procedures. The clip comprises two leg members 11 and 12 joined at their proximal end by a hinge section 13. The leg members latch or lock at their distal ends 14 and 15. In FIG. 2 there is shown the clip of FIG. 1 in its closed position closing off the lumen of a blood vessel 16. The surgeon, when placing this clip, very often has to place it in an area that he cannot see and, hence, it is important that he feel the resistance of the hinged section and the latching mechanism; that is, the tactile feedback he desires in the surgical device. The surgeon also wants to hear an audible click when the leg member 11 deflects and catches the opposite leg member 12. Another thermally formed surgical device is shown in FIG. 3. This device is a 2-piece fastener 20 for closing wounds and the like. The fastener comprises a staple 21 and a receiver 22 for the staple. In FIG. 4, there is shown yet another thermally formed device 25 for closing wounds, whether they be in the skin or fascia or even in the muscle. This device comprises a thin extended section 26 which has cross pieces 27 disposed at each end of the thin extended section. Using a suitable instrument which has a hollow needle for holding the device, the needle is inserted through tissue and the device used to close the wound with the extended section 26 spanning the wound area and the cross pieces 27 gripping opposite sides of the wound area as shown in FIG. 5.

Other medical devices which are contemplated within the present invention are solid products such as clips, staples, buttons, snaps, and the like.

The in vivo strength properties of the surgical devices contemplated by the present invention are extremely important. It is critical that the surgical device maintain its desired functional properties for extended periods of time when it is placed in an environment where it is slowly being absorbed, such as living tissue. The device must maintain its strength in such an environment for a sufficient period of time to allow it to perform the desired task. Our new devices in accordance with the present invention have excellent in vivo properties as will be further exemplified in the following specific example.

EXAMPLE

A number of injection molded clips are molded as described in co-pending commonly assigned patent application, Ser. No. 288,275 filed July 31, 1981. The clips have the configuration as shown in FIG. 1 and are treated in accordance with the present invention. The clips are scoured in two 15 minute isopropanol baths with stirring. In the scouring process, approximately 1 milliliter of isopropanol is used per clip. The alcohol is poured off and a single layer of clips is placed in a flat dish and dried in an ambient vacuum for 16 hours to remove the alcohol. Twenty scoured clips are removed, their density is determined and the clips are tested for opening strength and hinge strength.

The density is determined using a gradient density column prepared according to ASTM Method D-1505. (The gradient used extends from a density of 1.350 to 1.400 to cover the general range observed for polydioxanone clips.) Standard calibrated density floats are added to the column, graduated in millimeters, and allowed to sink to various positions in the gradient column. The density and position of each standard density float is recorded. A plot of density versus column position is constructed and a linear relationship is produced. Three clips are placed in the gradient density column and allowed to settle for 5 to 10 minutes. The clip positions are recorded. The average of the clip's positions is determined. The corresponding clip density is determined by the linear relationship of density to column position.

The hinge strength of the clip is the force required to break the clip at the hinge area and is determined as follows. The latching mechanism at the distal ends of the clip is cut away and the cut ends of the leg members placed in the opposite jaws of an Instron Tensiometer. The jaws are steel faced. Using a strain rate of 5 mm/min., the jaws are moved apart and the force necessary to break the hinge is determined in kilograms. The opening strength of the clip is the force required to open the clip after it has been closed and is determined as follows. The clip is closed over two aligned strips of Mylar polyester film. The strips are 4 mm wide, 178 mm long and 0.076 mm thick. The strips are separated at the ends and bent into opposed U-shape configurations. The ends of one of the U-shaped strips are placed in the jaw of an Instron Tensiometer while the ends of the opposite U-shaped strip are placed in the opposite jaw of the Instron Tensiometer. The jaws are steel faced. Using a strain rate of 5 mm/min. the jaws are moved apart and the force necessary to open the clip is determined in kilograms.

The crystallinity of the clip is measured as previously described.

The remaining clips are heat treated by placing them in an oven. Nitrogen is passed over the clips at a rate of 250 cubic feet per minute at ambient temperature. The temperature in the oven is then increased to 85° C. and maintained at that temperature at a nitrogen flow of 50 cubic feet per minute. After 8 hours and 16 hours, clips are removed and placed into a desicator jar and transferred to an ambient vacuum for cooling. The clips are packaged in foil pouches, ten clips per pouch. The pouches are ethylene oxide sterilized, degassed and sealed in a dry nitrogen atmosphere. The density and crystallinity of the clips are determined and the clips are tested for opening and hinge strength. The results of the tests are provided in the following Table 1.

TABLE 1

|  | No Annealing | 8 Hours Annealing | 16 Hours Annealing |
|---|---|---|---|
| % Crystallinity | 38 | 47 | 46 |
| Density (gms/cc) | 1.3829 | 1.3876 | 1.3881 |
| Opening Strength (kgms) | 2.30 | 2.30 | 2.43 |
| Hinge Strength (kgms) | 1.73 | 2.13 | 2.14 |
| Audible/Tactile Response | None | Distinct | Distinct |

As may be seen from the above table the clips treated in accordance with the present invention have a greater crystallinity, are denser and have improved strengths over the untreated clips.

Some of each type of clip; i.e., not annealed, annealed for 8 hours and annealed for 16 hours, are tested for in vivo strength retention properties. The in vivo strength properties are determined as follows. Packages containing clips from each submitted lot are opened and the clips removed. The clips are separated without apparent bias into groups consisting of 10 clips each. Each group will correspond to one hinge strength test interval. Special Long Evans rats, weighing 150 to 300 grams, are acclimated for a minimum of one week prior to surgery. Each rat is prepared for surgery, then anesthesized, and 2 clips are implanted in each rat. The clips are implanted in the left and right posterior dorsal subcutis of the rat. At each postimplantation period, 5 rats are euthanatized and the clips carefully removed. The hinge strength of the clips is determined by cutting away the latching mechanism at the distal end of the clip and placing the cut ends of the leg members in the opposing jaws of an Instron Tensiometer. The jaws are steel faced. Using a strain rate of 5 mm/min the jaws are moved apart and the force necessary to break the hinge is determined in kilograms. The results of the tests are provided in the following Table 2.

TABLE 2

| Length of Implanted Time | Hinge Strength Retention (Kg.) | | |
| --- | --- | --- | --- |
|  | No Annealing | 8 Hours Annealing | 16 hours Annealing |
| Baseline | 1.72 | 2.20 | 2.11 |
| 3 days | 1.66 | 2.00 | 2.01 |
| 10 days | 1.62 | 1.99 | 1.93 |
| 21 days | 0.92 | 1.73 | 1.76 |
| 28 days | 0 | 1.18 | 1.50 |

The above results clearly show the substantial unexpected improvement in the in vivo properties of clips treated in accordance with the present invention.

It should be pointed out that if you restrain the thermally formed device while treating it according to our annealing process, residual stresses will be "frozen" into the device. Once the stress is "frozen" in the product, the device will be weak in the area of the stress. In most configurations of a thermally formed device, the "frozen" stresses and, hence, the weakened areas will occur in the portions of the device requiring the greatest strength or the portions of the device subjected to the greatest forces or working during use. For example, in the clip configuration shown in FIG. 1, the portions of the clip requiring the greatest strength or workability are the hinge portion 13 and the latch portion 14. If stresses are frozen into the clip during the annealing process, these critical portions of the clip are weakened.

The fact that the temperature and time used in the annealing process of the present invention overlaps the temperature and time ranges used in annealing molecular oriented p-dioxanone polymers held under restraint is merely coincidental and totally unexpected.

Having now described the present invention including certain specific embodiments, it should be apparent to those skilled in the art that there may be various modifications and alterations to the present invention without departing from the spirit and scope of the present invention.

We claim:

1. A thermally formed, substantialy unoriented, annealed surgical device, said device having a resilient portion which provides the device with tactile properties and an interengaging portion which provides the device with audible properties, said device made of a polymer prepared from a monomer having the formula

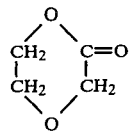

said device having a density of at least 1.3845 grams per cubic centimeter, a crystallanity of at least 43% and said device having improved audible and tactile properties.

2. A thermally formed, substantially unoriented, annealed surgical device, said device having a resilient portion which provides the device with tactile properties and an interengaging portion which provides the device with audible properties, said device made from a polymer having units of the formula:

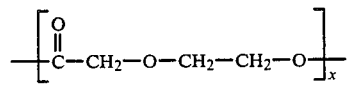

wherein x is the degree of polymerization resulting in a thermally formable device, said device having a density of at least 1.3845 grams per cubic centimeter, a crystallinity of at least 43%, and improved audible and tactile properties.

3. A device according to claim 1 or 2 having a crystallinity of at least 45%.

4. A device according to claim 1 or 2 wherein the device is a ligating clip.

5. The ligating clip of claim 4 comprising a pair of leg members connected at their proximal ends by a hinge section.

6. The ligating clip of claim 5 wherein the distal ends of the leg members include latching means.

7. The thermally formed device of claim 1 or 2 wherein the device is an injection molded device.

8. The ligating clip of claim 5 wherein the clip is an injection molded clip.

* * * * *